United States Patent
Zou et al.

(10) Patent No.: US 10,898,109 B2
(45) Date of Patent: Jan. 26, 2021

(54) METHOD AND DEVICE FOR AUTOMATIC IDENTIFICATION OF MEASUREMENT ITEM AND ULTRASOUND IMAGING APPARATUS

(71) Applicant: SHENZHEN MINDRAY BIO-MEDICAL ELECTRONICS CO., LTD., Shenzhen (CN)

(72) Inventors: Yaoxian Zou, Shenzhen (CN); Bin Yao, Shenzhen (CN); Yi Wei, Shenzhen (CN); Muqing Lin, Shenzhen (CN); Zuoqi Zeng, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 386 days.

(21) Appl. No.: 15/271,095

(22) Filed: Sep. 20, 2016

(65) Prior Publication Data

US 2017/0007161 A1 Jan. 12, 2017

Related U.S. Application Data

(63) Continuation of application No. PCT/CN2014/073777, filed on Mar. 20, 2014.

(51) Int. Cl.
*A61B 5/107* (2006.01)
*A61B 8/08* (2006.01)
(Continued)

(52) U.S. Cl.
CPC .......... *A61B 5/1075* (2013.01); *A61B 5/7267* (2013.01); *A61B 8/08* (2013.01);
(Continued)

(58) Field of Classification Search
CPC ..... A61B 5/1075; A61B 8/5223; A61B 8/469; A61B 8/08; A61B 5/7267; A61B 8/0866;
(Continued)

(56) References Cited

U.S. PATENT DOCUMENTS 5,588,435 A * 12/1996 Weng ............... A61B 8/0866
600/443
5,605,155 A * 2/1997 Chalana ............ A61B 5/1075
600/443
(Continued)

FOREIGN PATENT DOCUMENTS

CN 101 522 107 9/2009
CN 102151149 A 8/2011
(Continued)

*Primary Examiner* — Sanjay Cattungal
(74) *Attorney, Agent, or Firm* — Kory D. Christensen

(57) ABSTRACT

A method for automatic identification of a measurement item is provided. The method comprises acquiring, via an image acquisition module, gray values of pixels of a specified section image corresponding to ultrasonic echoes generated by reflection of ultrasound waves by a tissue under examination; identifying, via an identification module, at least one measurement item corresponding to the specified section image based on the gray values of the pixels; and measuring, via a measuring module, a measurement item parameter of the specified section image based on the measurement item identified. Because the measurement item of a specified section image can be automatically identified based on the content thereof, the user does not need to move a trackball to select measurement items, and therefore efficiency is increased.

24 Claims, 3 Drawing Sheets

(51) Int. Cl.
    *A61B 8/00*           (2006.01)
    *A61B 5/00*           (2006.01)
    *G06T 7/00*           (2017.01)
    *G06T 7/60*           (2017.01)

(52) U.S. Cl.
    CPC .......... *A61B 8/0866* (2013.01); *A61B 8/0875* (2013.01); *A61B 8/4461* (2013.01); *A61B 8/469* (2013.01); *A61B 8/5223* (2013.01); *G06T 7/0012* (2013.01); *G06T 7/60* (2013.01)

(58) Field of Classification Search
    CPC ... A61B 8/0875; A61B 8/4461; G06T 7/0012; G06T 7/60; G16H 50/30
    USPC .................................................. 600/437–469
    See application file for complete search history.

(56) References Cited

U.S. PATENT DOCUMENTS

| | | | | |
|---|---|---|---|---|
| 6,258,033 B1 * | 7/2001 | Grenon | ..................... | A61B 8/06 600/458 |
| 6,561,980 B1 * | 5/2003 | Gheng | ..................... | A61B 8/12 600/443 |
| 6,733,454 B1 * | 5/2004 | Bakircioglu | ............. | A61B 8/06 600/453 |
| 7,563,229 B2 * | 7/2009 | Heimdal | ................... | A61B 8/08 600/437 |
| 8,840,557 B2 * | 9/2014 | Casciaro | .............. | A61B 8/5223 600/443 |
| 8,879,813 B1 * | 11/2014 | Solanki | .................... | A61B 3/14 382/128 |
| 2002/0102023 A1 * | 8/2002 | Yamauchi | ................ | G06T 7/12 382/199 |
| 2006/0064016 A1 * | 3/2006 | Demi | ....................... | A61B 8/14 600/450 |
| 2006/0173317 A1 * | 8/2006 | Lee | ....................... | A61B 8/0883 600/437 |
| 2009/0093717 A1 * | 4/2009 | Carneiro | ................ | G06F 19/00 600/443 |
| 2011/0257529 A1 | 10/2011 | Casciaro et al. | | |
| 2013/0231564 A1 | 9/2013 | Zagorchev et al. | | |
| 2018/0085043 A1 * | 3/2018 | Panicker | ................ | A61B 8/486 |
| 2020/0302596 A1 * | 9/2020 | Yoo | ............................ | G06T 7/11 |

FOREIGN PATENT DOCUMENTS

| | | |
|---|---|---|
| CN | 102247172 | 11/2011 |
| CN | 102274051 A | 12/2011 |
| WO | 2010057665 A1 | 5/2010 |
| WO | 2012025889 | 3/2012 |

* cited by examiner

METHOD AND DEVICE FOR AUTOMATIC IDENTIFICATION OF MEASUREMENT ITEM AND ULTRASOUND IMAGING APPARATUS

TECHNICAL FIELD

The present disclosure relates to medical equipment, in particular to an ultrasound imaging apparatus and a method and device for automatic identification of a measurement item thereof.

BACKGROUND

Ultrasound imaging apparatus are generally used by a doctor to inspect tissues inside a human body. The doctor can place an ultrasound probe onto the surface of the skin corresponding to a tissue to obtain ultrasound images of the tissue. Due to its characteristics of safety, convenience, non-invasion and low cost, etc., ultrasound imaging has become a main assisting means for diagnosis.

In order to obtain measurements of an object of interest, the doctor needs to perform many measuring operations during the ultrasound examination. Since there are generally a plurality of measurement items which need to be measured for a tissue being examined in one measuring mode, while the measuring is a process in which the user needs to constantly interact with the apparatus, the user needs to constantly select the measurement item and then move a trackball to perform the measuring, which is time-consuming. For example, in an abdomen mode, the common measurement items include the size of the liver, gallbladder, spleen and kidneys, etc. In an obstetric mode, head circumference (HC), biparietal diameter (BPD), abdominal circumference (AC) and femur length (FL) are necessary measurement items for each examination. Generally, during an examination, the doctor may obtain a standard section image and then press a button for measuring, causing a measurement menu to be displayed by the apparatus. Next, the doctor may move the trackball to select a desired measurement item in the menu, and then the measuring of the selected measurement item can be performed. For example, in an obstetric examination, after obtaining a corresponding standard section image, the doctor first presses the button for measuring to open the measurement menu, and then moves the trackball to select a desired measurement item in the menu. Taking the head circumference as an example, the doctor first rotates the trackball to move the cursor to the measurement menu, and selects the measurement item of head circumference in the menu. After the measurement item is selected, the doctor rotates the trackball to move the cursor to a position at one side of the skull ring in the section image and presses a button for confirmation to determine a first point, and then moves the cursor to the other side and presses the button for confirmation to determine a second point, thereby obtaining one axis of an ellipse. Then, the doctor can move the cursor to adjust the length of the other axis of the ellipse and probably adjust the two points determined, until the ellipse matches the skull of the fetus. Therefore, in one measuring, many points need to be determined in order to match the ellipse with the structure to be measured. In the case where the object to be measured is linear, at least two points need to be determined. It was reported that a doctor will spend 20% to 30% of the time on measuring.

Certain methods for automatic measurement have been proposed in some patents or publications in order to save the measuring time of the doctor. However, in these methods, the user needs to manually select the corresponding measurement item in the menu according to the obtained section image and then perform an automatic or semi-automatic measuring, which will directly affect the degree of automation of the automatic measuring. Furthermore, the operations of the doctor on the measurement item will affect the measuring time. Moreover, the doctor usually does not like the distraction of constantly pressing the button and selecting items in the menu during the examination.

SUMMARY

According to an aspect of the present disclosure, a method for automatic identification of a measurement item is provided. The method may include:

acquiring gray values of pixels of a specified section image, wherein the gray values of the pixels correspond to ultrasound echoes generated by reflection of ultrasound waves by a tissue under an examination;

identifying at least one measurement item corresponding to the specified section image based on the gray values of the pixels; and measuring a measurement parameter of the specified section image based on the measurement item identified.

According to another aspect of the present disclosure, an ultrasound imaging apparatus is provided. The apparatus may include a probe which transmits ultrasound waves to a tissue and receives ultrasound echoes, a signal processor which processes the ultrasound echoes to generate ultrasound image data, and an image processor which processes the ultrasound image data and generates section images. The image processor may be further configured to:

acquire gray values of pixels of a specified section image, wherein the gray values of the pixels correspond to ultrasound echoes generated by reflection of ultrasound waves by a tissue under an examination;

identify at least one measurement item corresponding to the specified section image based on the gray values of the pixels; and measure a measurement parameter of the specified section image based on the measurement item identified.

Based on the method/device for automatic identification of a measurement item provided by the present disclosure, the measurement items of a specified section image can be automatically identified based on the contents of the specified section image, such that the user does not need to select the measurement items during the measurement, and thereby the measurement is more convenient and automatic.

DETAILED DESCRIPTION

Figure 1:
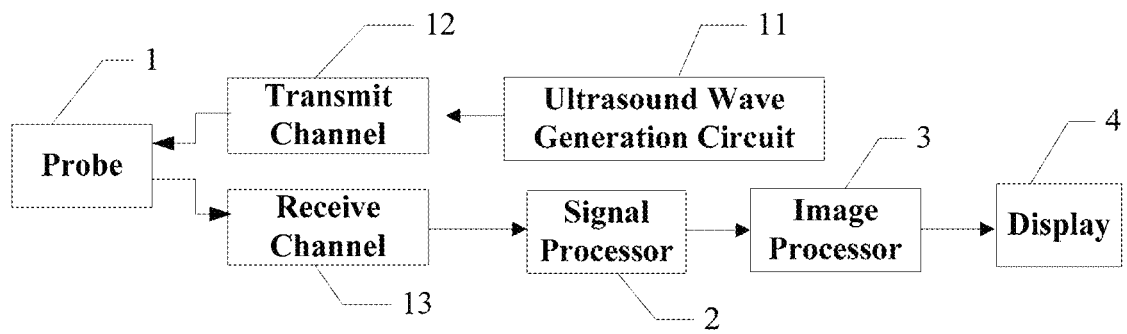
FIG. 1 schematically shows an ultrasound imaging apparatus according to an embodiment of the present disclosure.

Medical ultrasound imaging is generally used by doctors to inspect tissues inside the human body. The doctor can place an ultrasound probe onto the surface of the skin to obtain ultrasound section images of the tissue below the skin. Referring to FIG. 1, which shows the structure of an ultrasound imaging apparatus, the ultrasound imaging apparatus may include an ultrasound wave generation circuit 11, a probe 1, a signal processor 2, an image processor 3 and a display 4.

The probe 1 may transmit ultrasound waves to a scanning object and receive the ultrasound echoes. The ultrasound wave generation circuit 11 may generate waveform data and excite transducers of the probe 1 by a transmit channel 12 to transmit ultrasound waves to the tissue to be examined. After the reflection and absorption of the ultrasound waves, the ultrasound echoes can be formed. The probe 1 may receive the ultrasound echoes and output them to the signal processor 2 through a receive channel 13.

The signal processor 2 may process the ultrasound echoes to generate ultrasound image data. The signal processor 2 may perform beam-forming on the ultrasound echoes received through the receive channel 13 to obtain radio frequency signals, and then perform quadrature demodulation on the radio frequency signals to obtain quadrature demodulated baseband signals. The processed ultrasound image data may be output to the image processor 3.

The image processor 3 may process the ultrasound image data and generate the section images, and send the section images to the display 4 for displaying. The image processor 3 may include a device for automatic identification of measurement items, which may process the ultrasound image data output by the signal processor 2 to identify the measurement items corresponding to the section image specified by the user, and further perform the measuring of the measurement parameters corresponding to the measurement items.

The display 4 may display the section images generated by the image processor 3 and the measurement parameters.

Figure 2:
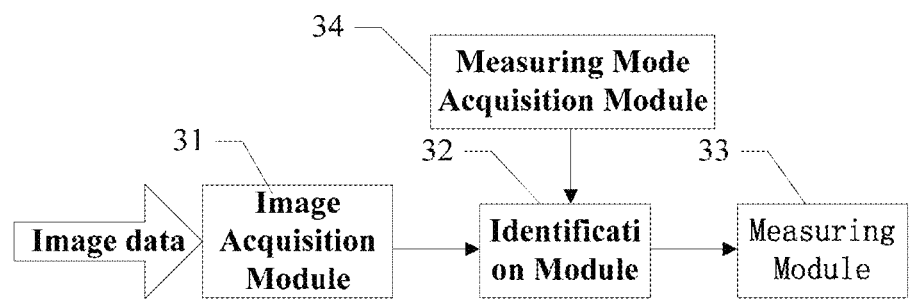
FIG. 2 schematically shows a device for automatic identification of a measurement item according to an embodiment of the present disclosure.

FIG. 2 schematically shows the structure of the device for automatic identification of measurement items, which may include an image acquisition module 31, an identification module 32 and a measuring module 33.

The image acquisition module 31 may acquire the gray value of the pixels in the specified section image. The gray value of the pixels may correspond to the ultrasound echoes generated by the reflection of the ultrasound waves by the tissue being examined.

The identification module 32 may identify at least one measurement item corresponding to the specified section image based on the gray value of the pixels. For example, the identification module 32 may process the gray values of the pixels and perform a comparative analysis with a preset data model, and identify the measurement item according to the result of the analysis.

The measuring module 33 may perform measuring on the specified section image to obtain the measurement parameters based on the identified measurement item.

In another embodiment, the device for automatic identification of measurement items may further include a measuring mode acquisition module 34, which may acquire the measuring mode selected by the user. The identification module 32 may identify the measurement items corresponding to the specified section image according to the measuring mode selected by the user during the identification of the measurement items.

Figure 3:
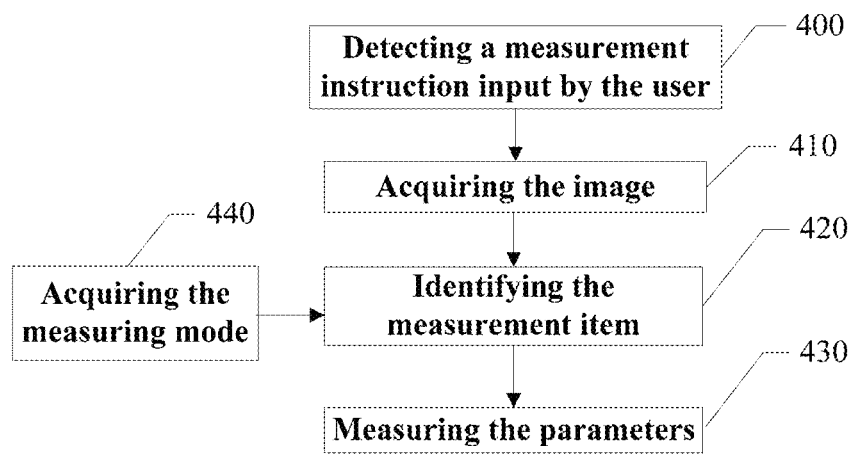
FIG. 3 is a flow chart of a method for automatic identification of a measurement item according to an embodiment of the present disclosure.
Figure 4:
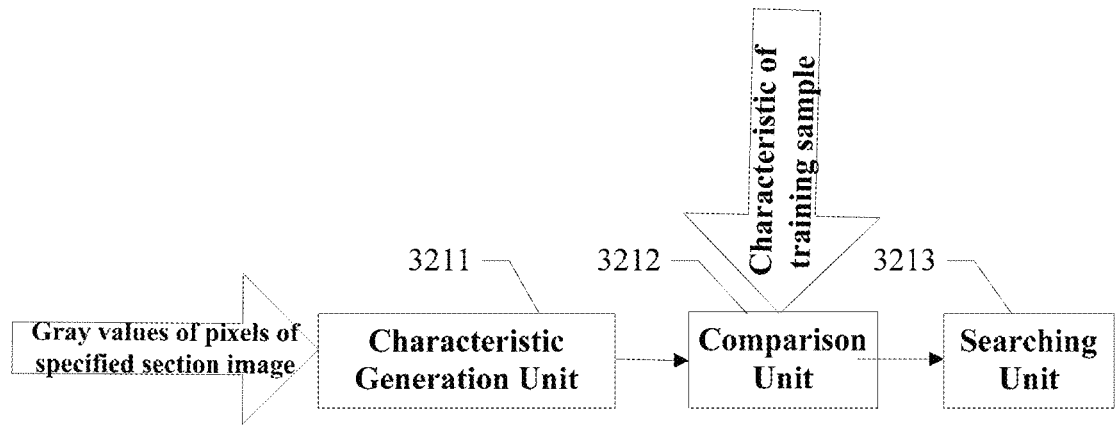
FIG. 4 schematically shows an identification module provided by embodiment 1 of the present disclosure.

A flow chart of a method for automatic identification of measurement items using the ultrasound imaging apparatus described above is shown in FIG. 3. The method may include following steps.

Step 400: detecting a measurement instruction input by the user. The measurement instruction may be generated by the user by pressing a button for measuring or selecting a measurement item. When a measurement instruction is detected, the following steps may be performed.

Step 410: acquiring the image. The image processor may send the processed ultrasound image data to the display, where the processed ultrasound image data may be displayed. The user may specify a section image by observing the displayed images. According to the section image specified by the user, the gray values of pixels in the specified section image may be acquired from stored image data. The specified section image may generally be the section image which is presently displayed. The gray value of the pixels may correspond to the ultrasound echoes formed by the reflection of the ultrasound signals by the tissue. The ultrasound echoes of bones are strong, and the corresponding image has a great gray value. The ultrasound echoes of soft tissue are weak, and the corresponding image has a small gray value.

Step 420: identifying the measurement item. In one measuring mode, for the tissue being examined, there may generally be a plurality of measurement items which need to be measured. For example, in an abdomen measuring mode, the common measurement items may include the size of the liver, gallbladder, spleen and kidneys, etc. In an obstetric measuring mode, the common measurement items may include head circumference (HC), biparietal diameter (BPD), abdominal circumference (AC) and femur length (FL), etc. In other embodiments, there may be other measuring modes, and thus there may correspondingly be other corresponding measurement items. The measurement items may be determined according to the section image of the object to be measured. There are always differences between the section images corresponding to different measurement items, and these differences make the automatic identification possible. One possible solution is presetting data modes of section images corresponding to the plurality of measurement items in the apparatus and identifying the measurement item by comparing the gray values of pixels in the specified section image with the preset data modes. The preset data modes may be the characteristics which are able to distinguish a certain section image from other section images, such as a training sample mode. The preset data modes may also be the physical characteristics (such as the shape, the brightness range or the size, etc.) of the sections corresponding to the measurement items. When the section image of a measurement object is determined, the measurement items for this measurement object are determined. On the contrary, when the measurement items are determined, the section image of the measurement object corresponding to these measurement items needs to be displayed. For example, for the obstetric examination, the head circumference and the abdominal circumference are elliptic objects, the biparietal diameter and the femur length are linear object, and the head circumference and the biparietal diameter can be measured in a same section. Therefore, these four measurement items may correspond to three measurement sections: the head circumference section (HC and BPD may correspond to a same section), the abdominal circumference section and the femur section. When the section image specified by the doctor is an abdominal circumference section, the measurement item may be the abdominal circumference (AC); when the specified section image is a femur section, the measurement item may be the femur length (FL); and when the section image specified by the doctor is the head circumference section, the measurement items may be the head circumference (HC) and/or the biparietal diameter (BPD). Accordingly, in the present embodiment, the image processor may process and analyze the gray values of the pixels to identify the type of the current specified section image, and thereby identify the measurement items corresponding to this specified section image.

Step 430: measuring the parameters. Based on the measurement items identified in the step 420, the parameters corresponding to the measurement items of the specified section image may be measured. In the actual measurement process, the parameters may be measured manually, semi-automatically or automatically. When a certain section image corresponds to two or more measurement items (for example, the measurement items of the head circumference section may include the head circumference (HC) and the biparietal diameter (BPD)), the measurement items identified may be measured one by one.

In other embodiments, the method may further include the following steps before identifying the measurement items in the step 420.

Step 440: acquiring the measuring mode adopted during the examination of the tissue. In this step, the measuring mode selected by the user may be acquired, which can reduce the identification range of the measurement items, and thereby not only may the identification efficiency be increased, but the identification accuracy may also be improved.

In the embodiments of the present disclosure, the measurement items can be identified automatically based on the images, such that the doctor need not select the measurement item in the menu by moving the trackball, and thereby the efficiency of the measuring can be increased.

In the embodiments of the present disclosure, solutions for automatic identification of the measurement items may be added. These solutions may be implemented in a plurality of ways that will be further described in detail with reference to specific embodiments.

Embodiment 1

Figure 5:
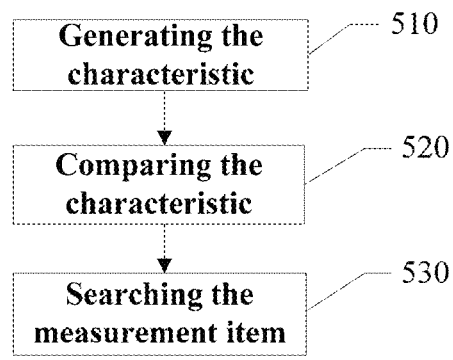
FIG. 5 is a flow chart of an identification method provided by embodiment 1 of the present disclosure.

Differences exist between sections corresponding to different measurement items. Based on this fact, in the present embodiment, characteristics which can indicate the section corresponding to certain measurement items may be extracted, and the measurement items may be identified based on the characteristics. In one embodiment, the characteristics of the sections may be extracted and classified using a machine learning method. Referring to FIG. 5, an identification module of the present embodiment is shown, which may include a characteristic generation unit 3211, a comparison unit 3212 and a searching unit 3213.

The characteristic unit 3211 may generate the characteristics of the specified section image using the gray values of the pixels in the specified section image. The comparison unit 3212 may compare the characteristics of the specified section image with the characteristics of training samples of a preset training sample mode. The searching unit 3213 may search the training sample whose characteristics are most similar to the characteristics of the specified section image, and output the measurement items corresponding to the training sample searched as the corresponding measurement items corresponding to the specified section image.

Based on the identification module above, the present embodiment further provides a machine learning identification method. The machine learning method generally generates the characteristics of a plurality of samples by the information of training samples (a series of samples for which the measurement items are known) and compares the characteristics of the section sample to be measured with the characteristics of the training samples to determine which type of measurement items the section sample to be measured corresponds to. In the art, common machine learning methods may include principal component analysis (PCA) method, linear discriminant analysis (LDA) method, kernel principal component analysis (KPCA) method, locality preserving projections (LPP), support vector machine (SVM) method and artificial neural networks (ANNs), etc.

Generally, the dimensionality of the image data acquired by the image acquisition module is very high. An image with sizes of W*H may be considered as a W*H-dimensional vector. A great relevance generally exists between the dimensions of this high-dimensional vector. In other words, the expression of high-dimensional data has great redundancy. One common method is projecting the high-dimensional data to a low-dimensional space to eliminate the redundancy between the dimensions of the data. PCA is this kind of method, of which the essence is finding out the projection which best represents the original high-dimensional data in the sense of least mean square. The present embodiment will be further described taking PCA as an example. However, a person ordinarily skilled in the art will understand that, in other embodiments, the technical solutions of the present embodiment may also be implemented using other machine learning methods (such as LDA, KPCA, LPP, SVM, or ANNs, etc.) according to the concept of the present embodiment without creative work.

Referring to FIG. 5, a method for identification using the identification module above may include following steps.

Step 510: generating the characteristics. In this step, the characteristics of the specified section image may be generated using the gray values of the pixels of the specified section image.

In the present embodiment, the measurement items of the specified section image may be obtained by comparing the characteristics of the specified section image with the characteristics of the preset training samples. Therefore, first, the characteristics of the training samples and the characteristics of the specified section image may be acquired. In an embodiment, the characteristics of the training samples and the characteristics of the specified section image may be the eigenvalues, the eigenvectors or a combination of the eigenvalues and the eigenvectors. In an embodiment, the characteristic of the training sample may be the projection coefficient of the eigenvectors of the training sample on the mean value of the training sample, and the characteristic of the specified section image may be the projection coefficient of the eigenvectors of the specified section image on the mean value of the training sample. The advantage of this embodiment is that the high-dimensional data is projected to the low-dimensional space and the redundancy between the dimensions of the data is eliminated, such that the calculation is reduced and the computational efficiency is increased.

For a training sample library, assuming that this training sample library includes N training samples, the image of each training sample has a resolution of W×H, and each image is expanded into a M-dimensional long vector (where M=W×H), the image of this training sample library can be expressed as an M×N matrix, which can be expressed as $[I_1, \ldots, I_N]_{M \times N}$, where $I_i$ is a training sample vector.

First, the mean value of the sample (which is referred to as the mean sample hereinafter) may be calculated:

$$m = \frac{\sum_{i=1}^{N} I_i}{N}$$

here m is the mean sample. New training samples with a mean value of zero may be obtained by subtracting the samples in the training sample library with the mean sample:

$$L=[I_1-m, \ldots, I_N-m]$$

The covariance matrix of the new training samples may be:

$$C = \sum_{i=1}^{N} (I_i - m)(I_i - m)^T = LL^T$$

where $L^T$ is the transpose of matrix L.

After the covariance matrix C of the new training samples is obtained, the eigenvalues of the matrix C may be calculated. Because the matrix C has too-large dimensions, it is very difficult to calculate the eigenvectors of the matrix C directly. Therefore, the eigenvectors of a small matrix $R=L^TL$ may be calculated first.

Assuming that V is the eigenvector matrix of the small matrix R and A is the eigenvalue matrix, then:

$$(L^T L)V = VA$$

Both sides of the equation may be multiplied by L to obtain:

$$(LL^T)LV = LVA$$

Therefore, the orthogonalized eigenvector of the matrix $C=LL^T$ may be:

$$E=LVA^{1/2}$$

where the eigenvalue matrix A may be a M*M diagonal matrix and the eigenvalues may be arranged in descending order, i.e., $\Lambda_{11} \geq \Lambda_{22} \geq \ldots \Lambda_{MM}$, where $\Lambda_{jj}$ represents the element of the eigenvalue matrix $\Lambda$ at j-th column and j-th row.

Actually, most of the eigenvalues are very small, even zero. Therefore, it is possible for only larger eigenvalues and corresponding eigenvectors to remain. For example, only the first n eigenvalues, and only the first n columns of the eigenvectors V, are remained. In other words, the dimensionality of the remaining eigenvectors V is N*n and n may be determined in a plurality of ways. For example, n may be a preset constant. Or, n may be a value which leads to $$\sum_{i=1}^{n} \Lambda_{ii} \geq P \sum_{i=1}^{M} \Lambda_{ii},$$

where P is a percentage. For example, P=95% means that 95% of the characteristics of the original data are remained.

Then, the projection of the training samples on the mean sample (i.e., the characteristics or principal component of the training samples) may be obtained by:

$$F_i = E^T(I_i - m) \qquad (1)$$

where $E^T$ is the transpose matrix of the matrix E, and $F_i$ is the characteristic of $I_i$. This projection reduces the dimensionality of the sample from M*1 to n*1 and eliminates the correlation between the high-dimensional data. This n*1-dimensional data can best represent the original data in the sense of least mean square.

A person ordinarily skilled in the art will understand that the calculation of the step above to the sample library can be performed offline, and the results of the calculation (for example, the characteristics $F_i$ of the matrix E and the training samples) may be stored in the apparatus.

For a specified section image, the gray values of all pixels of the section image may be acquired, which may be similarly expanded into an M-dimensional vector $I_{test}$. The characteristic of the specified section image may be calculated according to the formula (2):

$$w = E^T(I_{test} - m) \qquad (2)$$

where w is the projection coefficient of the eigenvectors of the section image on the mean value of the training sample (i.e., the characteristic of the section image), $I_{test}$ is the eigenvectors of the section image, m is the mean value of the training samples, E is the orthogonalized eigenvector, and $E^T$ is the transpose matrix of the matrix E.

Step 520: comparing the characteristics. In this step, the characteristics of the specified section image may be compared with the characteristics of the plurality of training samples of the preset training sample mode.

The characteristics of the specified section image calculated by the formula (2) in the step 510 may be compared with the characteristics of the plurality of training samples of the preset training sample mode as defined by the formula (1) to obtain:

$$x_i = \|w - F_i\|$$

where $x_i$ is the modulus of the comparison result of the characteristic of the specified section image with the characteristic of the i-th training sample $F_i$, where $1 \leq i \leq N$. In an embodiment, the characteristic of the specified section image may be compared with the plurality of samples in the training sample library.

Step 530: searching the measurement items. In this step, the training sample with characteristics most similar to the characteristics of the specified section image may be searched. The measurement items corresponding to the training sample which is searched may be the measurement items of the specified section image.

After the comparison of the characteristics of the specified section image with the characteristics of the plurality of training samples of the preset training sample mode, the searching of the measurement items corresponding to the specified section image may be performed using the following formula:

$$ind = \text{index}\left(\min_{1 \leq i \leq N} x_i\right)$$

where the function index represents the serial number (i) corresponding to the minimum of $x_i$, which means that the i-th training sample is the one most similar to the sample being processed. Therefore, the measurement items of the sample being processed may be the same as the measurement items of the i-th training sample, which is known. Thereby, the measurement items corresponding to the specified section image are searched out.

Further, in other embodiments, different measuring modes may correspond to different sample modes which have different sample libraries. Therefore, before comparing the characteristics in the step 520, the measuring mode selected by the user may be acquired to make a selection on the sample libraries to reduce the number of samples included in the comparison, which not only can increase the identification efficiency, but also may further increase the identification accuracy.

Embodiment 2

Figure 6:
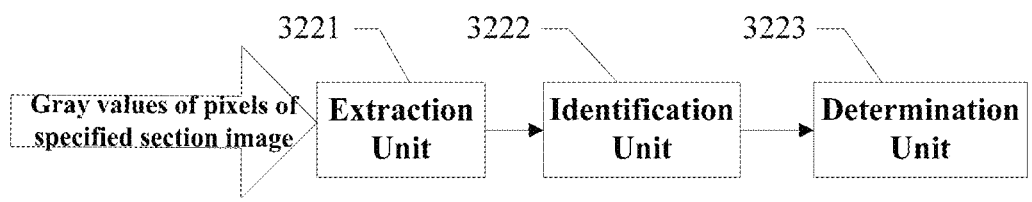
FIG. 6 schematically shows an identification module provided by embodiment 2 of the present disclosure.

The machine learning method needs to acquire the characteristics of a plurality of training samples and then perform the comparison. Therefore it may be necessary to acquire as many training samples as possible, and these training samples should cover a variety of situations in position, size and shape, etc. In the case where there are not enough training samples, image processing methods may be used. In the present embodiment, image processing methods may be used to extract the image features (such as the gray values, shape or the like) of the section images to determine the measurement items. Referring to FIG. 6, an identification module provided in the present embodiment is shown. The identification module may include an extraction unit 3221, an identification unit 3222 and a determination unit 3223.

The extraction unit 3221 may extract the high intensity portion of the specified section image based on the gray values of the pixels of the specified section image. The identification unit 3222 may identify the high intensity portion based on the measuring mode to determine the section type of the specified section image. The determination unit 3223 may determine the measurement items corresponding to the specified section image based on the section type determined and the measurement items corresponding thereto.

The present embodiment also provides a method for identification of measurement items using the identification module above, which may extract the features (such as the gray values, shape or the like) of the section image and then perform the analysis and determination using these features.

Since the image features in different measuring modes may be different, the image processing methods used may vary with the measuring modes. For example, in the obstetric measuring mode, the common measurement items may include head circumference (HC), biparietal diameter (BPD), abdominal circumference (AC) and femur length (FL). The head circumference and the abdominal circumference are elliptic objects, the biparietal diameter and the femur length are linear objects, and the head circumference and the biparietal diameter can be measured in a same section. Therefore, these four measurement items may correspond to three measurement sections: the head circumference section (HC and BPD may correspond to a same section), the abdominal circumference section and the femur section. The head circumference section contains the skull of the fetus, which is represented as a high intensity portion in an ultrasound section image. Furthermore, the skull in the near field and the skull in the far field together form an ellipse, in which the brain of the fetus is located. The gray values within the ellipse are significantly lower than the gray values of the skull. In the femur section, the femur is also represented as a high intensity portion, but the femur is substantially linear and only has a few curved portions. In the abdominal circumference section, the abdominal circumference is represented as an elliptic object with great gradient. However, the boundary of the abdominal circumference is not represented as a high intensity portion, and the internal portion and the boundary of the abdominal circumference are close in gray value. Therefore, when the image processing methods are adopted to identify the measurement items, the measuring mode selected by the user may be acquired first, and then the image processing methods may be used to identify the measurement items.

Figure 7:
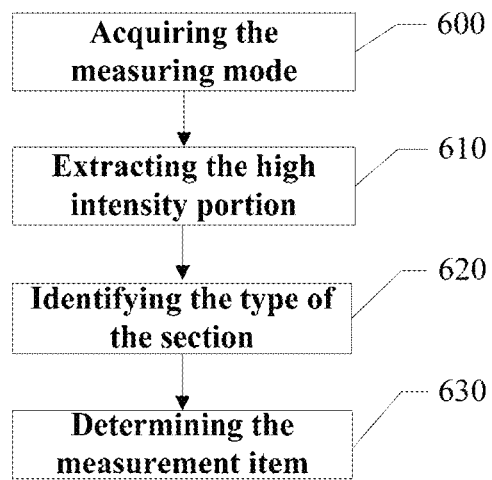
FIG. 7 is a flow chart of an identification method provided by embodiment 2 of the present disclosure.

Referring to FIG. 7, a flow chart of the identification process of the present embodiment is shown. The methods of the present embodiment will be further described hereinafter taking the obstetric measuring mode as an example. The methods may include the following steps.

Step 600: acquiring the measuring mode.

Step 610: extracting the high intensity portion. In this step, the high intensity portion in the specified section image may be extracted based on the gray values of the pixels of the specified section image.

In an embodiment, after the gray data of the specified section image is acquired, a preprocessing may be performed on the image and then the high intensity portion may be extracted based on the preprocessed image. The preprocessing may be mainly used to suppress the noise of the image, increase the continuity of the boundary and highlight the high intensity portion. There are many preprocessing methods, such as anisotropic smoothing, etc. In other embodiments, the preprocessing may not be performed and the high intensity portion may be extracted based on the original gray data of the image.

In an embodiment, a cluster segmentation method may be used to extract the high intensity portion in the specified section image. The gray values of the pixels of the specified section image may be categorized into a plurality of categories using the cluster segmentation method. The pixels with the gray values of the one or more categories with maximum gray value may be kept unchanged while the pixels with the gray values of other categories may be assigned with zero, thereby obtaining a characteristic image. For example, the gray values of the specified section image may be categorized into N categories (for example, N=3). The N categories may be arranged in descending order, and the first M categories (for example, M≥1 and M<N) may be determined as the category with maximum intensity (i.e., the high intensity portion). The pixels with the gray values of the following N-M categories may be assigned with zero while other pixels may be kept unchanged, thereby obtaining the characteristic image. Connected regions in the characteristic image may be identified, and one or more connected regions with maximum intensity may be determined, thereby obtaining the high intensity portion of the specified section image. In an embodiment, the first X connected regions of the connected regions arranged in descending order may be determined as the connected regions with maximum intensity. X may be preset by the apparatus, and generally may be 1~10. In other embodiments, X may be another value based on actual needs.

In an embodiment, the characteristic image may also be obtained by convoluting a preset M×N operator with the specified section image. The values of the elements in the operator may be determined based on actual needs.

Furthermore, the characteristic image may generally contain a lot of noise. Therefore, certain morphological operations (such as morphological corrosion, opening operation, removal of small areas or the like) may be performed on the characteristic image to remove the noise and increase the continuity of the boundaries in the image.

Step 620: identifying the type of the section. In this step, an identification method may be performed on the high intensity portion based on the measuring mode to determine the section type of the specified section image.

Figure 8A:
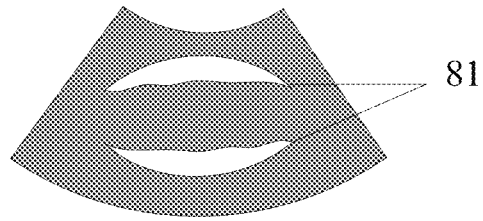
FIGS. 8a-c schematically show the measurement item section in the obstetric measuring mode according to embodiment 2, where FIG. 8a schematically shows the head circumference section, FIG. 8b schematically shows the abdominal circumference section, and FIG. 8c schematically shows the femur section.
Figure 8B:
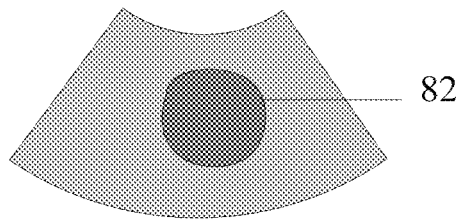
Figure 8C:
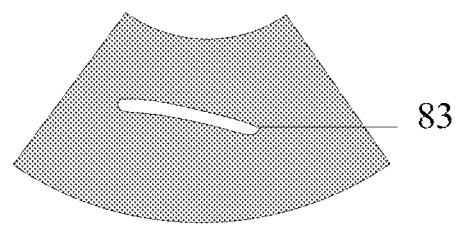

In obstetric measuring mode, both the head circumference and the abdominal circumference are substantially elliptic. The head circumference section (as shown in FIG. 8*a*) and the abdominal circumference section (as shown in FIG. 8*b*) mainly differ as follows. The head circumference section contains the skull 81, which is represented as high intensity echoes during ultrasound examination. Other tissues of the head, which are represented as low intensity portions during the ultrasound examination and are significantly different from the skull 81 in intensity, are located within the head circumference. Meanwhile, the abdominal circumference section contains the abdomen 82 of the fetus, which has a boundary of lower intensity than the head circumference, and within which the echoes are relatively uniform and not much different from those of the boundary. Both the head circumference and the femur section (as shown in FIG. 8*c*) contain bones with high intensity, of which the main difference is that the head circumference contains two symmetrical, arc-shaped bones of skull 81 while the femur section contains generally only one, relative straight bone 83. Based on the physical facts above, in this step, the intensity and shape of the connected regions identified may be analyzed and compared to determine which type of section the section image belong to.

In an embodiment, in a known measuring mode (for example, the obstetric measuring mode), an intensity threshold for the connected regions may be set in order to determine whether bones are contained in the section image. For example, in the case where the mean intensity of the connected regions is greater than a first threshold, the specified section image contains bones; in the case where the mean intensity of the connected regions is lower than a second threshold, the specified section image does not contain bones. The first threshold is greater than the second threshold. In other embodiments, it is also possible that only one intensity threshold for the connected regions is set.

A simple method for the analysis of the shape of the bones is using curvature to determine whether the bone bends and, if so, the degree of the bending. For example, in a known measuring mode (for example, the obstetric measuring mode), curvature thresholds may be set. In the case where the curvature of the connected regions is greater than a curvature threshold, the specified section image contains curved bone; in the case where the curvature of the connected regions is lower than a curvature threshold, the specified section image does not contain curved bone. In one embodiment, the curvature may be defined as the angle between two lines formed by respectively connecting the point located at the middle of the connected region and the points located at the both ends of the connected region. In other embodiments, the curvature may be defined in other ways as long as it can represent the degree of the bending of the connected regions.

For example, in the obstetric measuring mode, in the case where the mean intensities of the X connected regions are greater than a certain threshold, it is determined that the specified section image contains bones and the section may be the head circumference section or the femur section. Then, the curvature of the connected regions may be considered. In the case where the curvatures are greater than a certain threshold, it is determined that the bones contained in the section are curved and the specified section is the head circumference section. In the case where the curvatures are lower than a certain threshold, it is determined that the bones contained in the section are straight and the specified section is the femur section. In the case where the mean intensities of the X connected regions are all lower than a certain threshold, it is determined that the specified section does not contain bones with high intensity and is an abdominal section.

Step 630: determining the measurement items. In this step, the measurement items corresponding to the specified section image may be determined based on the section type determined and the measurement items corresponding thereto.

A person skilled in the art will understand that all or parts of the steps of the methods of the embodiments described above may be implemented by instructing related hardware using programs. The programs may be stored in a computer-readable storage medium which may include ROM, RAM, disk or CD, etc.

The present disclosure is described above with reference to specific embodiments. However, it is only used to facilitate the understanding of, but not limit, the present disclosure. Variations to the specific embodiments described above may be made by a person skilled in the art based on the concepts of the present disclosure.

What is claimed is:

1. A method for automatic identification of a measurement item, comprising:
   acquiring gray values of pixels of a specified section image, wherein the gray values of the pixels correspond to ultrasound echoes generated by reflection of ultrasound waves by a tissue under examination;
   automatically determining a section type of the specified section image based on one or more characteristics defined by the gray values of the pixels, the section type identifying a particular section of a particular area of the tissue from which the specified section image was acquired;
   obtaining a correspondence between the section type and one or more measurement items which are measurable in an image of the section type;
   automatically identifying at least one measurement item which is measurable in the specified section image according to the correspondence and the section type of the specified section image;
   detecting an object corresponding to the identified at least one measurement item in the specified section image; and
   obtaining a value of the identified at least one measurement item by performing a measurement on the detected object.

2. The method of claim 1, wherein the measurement item is identified based on a comparative analysis of the gray values of the pixels with a preset data mode.

3. The method of claim 2, further comprising acquiring a measuring mode used during tissue examination.

4. The method of claim 1, wherein automatically determining a section type of the specified section image based on one or more characteristics defined by the gray values of the pixels comprises:
generating a characteristic of the specified section image based on the gray values of the pixels of the specified section image;
comparing the characteristic of the specified section image with characteristics of training samples in a preset training sample mode, respectively; and
searching a training sample whose characteristic is most similar to the characteristic of the specified section image and determining section type of the training sample searched out as the section type of the specified section image.

5. The method of claim 4, wherein the characteristic of the training sample is a projection coefficient of an eigenvector of the training sample on a mean value of the training sample, and the characteristic of the specified section image is a projection coefficient of an eigenvector of the specified section image on the mean value of the training sample.

6. The method of claim 5, wherein the characteristic of the specified section image is calculated by the following formula:

$$w = E^T (I_{test} - m)$$

wherein $I_{test}$ is the eigenvector of the specified section image, m is the mean value of the training sample, T represents matrix transpose, E is an orthogonalized eigenvector, and w is the projection coefficient of the eigenvector of the specified section image on the mean value of the training sample.

7. The method of claim 3, wherein automatically determining a section type of the specified section image based on one or more characteristics defined by the gray values of the pixels comprises:
extracting high intensity portions from the specified section image based on the gray values of the pixels of the specified section image; and
performing an identification on the high intensity portions based on the measuring mode to determine the section type of the specified section image.

8. The method of claim 7, wherein extracting high intensity portions from the specified section image comprises:
categorizing the gray values of the pixels of the specified section image into a plurality of categories using a cluster segmentation method;
keeping pixels which have gray values of one or more categories with maximum gray values unchanged while assigning zero to pixels which have gray values of other categories to obtain a characteristic image; and
identifying connected regions in the characteristic image and determining one or more connected regions with maximum intensity to obtain the high intensity portions.

9. The method of claim 8, wherein performing an identification on the high intensity portions based on the measuring mode comprises:
analyzing intensities and shapes of the connected regions identified; and
determining the section type of the specified section image based on the measuring mode and results of the analysis.

10. The method of claim 1, wherein obtaining a value of the identified at least one measurement item comprises obtaining a value of the identified at least one measurement item manually, semi-automatically or automatically.

11. The method of claim 1, wherein the particular section of the section type corresponds to a direction along which a desired section image is acquired from the particular area of the tissue.

12. The method of claim 1, wherein automatically determining a section type of the specified section image based on one or more characteristics defined by the gray values of the pixels comprises:
extracting section type characteristics of the specified section image based on which one section type is distinguished with another section type; and
determining the section type of the specified section imaged based on the extracted section type characteristics.

13. The method of claim 1, wherein the determined section type is a head circumference section which contains a skull of a fetus, an abdominal circumference section which contains an abdomen of a fetus or a femur section which contains a thigh bone of a fetus.

14. The method of claim 1, wherein the one or more characteristics defined by the gray values of the pixels are a shape, a brightness range or a size define by the gray values of the pixels.

15. An ultrasound imaging apparatus, comprising:
a probe which transmits ultrasound waves to a tissue and receives ultrasound echoes;
a signal processor which processes the ultrasound echoes to generate ultrasound image data; and
an image processor which processes the ultrasound image data and generates section images;
wherein the image processor is further configured to:
acquire gray values of pixels of a specified section image, wherein the gray values of the pixels correspond to ultrasound echoes generated by reflection of ultrasound waves by a tissue under examination;
automatically determine a section type of the specified section image based on one or more characteristics defined by the gray values of the pixels, the section type identifying a particular section of a particular area of the tissue from which the specified section image was acquired;
obtain a correspondence between the section type and one or more measurement items which are measurable in an image of the section type;
automatically identify at least one measurement item which is measurable in the specified section image according to the correspondence and the section type of the specified section image;
detect an object corresponding to the identified at least one measurement item in the specified section image; and
obtain a value of the identified at least one measurement item by performing a measurement on the detected object.

16. The apparatus of claim 15, wherein the image processor is further configured to identify the measurement item based on a comparative analysis of the gray values of the pixels with a preset data mode.

17. The apparatus of claim 16, wherein the image processor is further configured to acquire a measuring mode used during tissue examination.

18. The apparatus of claim 15, wherein the image processor is further configured to:
generate a characteristic of the specified section image based on the gray values of the pixels of the specified section image;
compare the characteristic of the specified section image with characteristics of training samples in a preset training sample mode, respectively; and
search a training sample whose characteristic is most similar to the characteristic of the specified section image, and determine section type of the training sample searched out as the section type of the specified section image.

19. The apparatus of claim 18, wherein the characteristic of the training sample is a projection coefficient of an eigenvector of the training sample on a mean value of the training sample, and the characteristic of the specified section image is a projection coefficient of an eigenvector of the specified section image on the mean value of the training sample.

20. The apparatus of claim 19, wherein the image processor is configured to generate the characteristic of the specified section image using the following formula:

$$W = E^T(I_{test} - M)$$

wherein $I_{test}$ is the eigenvector of the specified section image, m is the mean value of the training sample, T represents matrix transpose, E is an orthogonalized eigenvector, and w is the projection coefficient of the eigenvector of the specified section image on the mean value of the training sample.

21. The apparatus of claim 17, wherein the image processor is further configured to:
extract high intensity portions from the specified section image based on the gray values of the pixels of the specified section image;
perform an identification on the high intensity portions based on the measuring mode to determine the section type of the specified section image.

22. The apparatus of claim 21, wherein the image processor is further configured to:
categorize the gray values of the pixels of the specified section image into a plurality of categories using a cluster segmentation method;
keep pixels which have gray values of one or more categories with maximum gray values unchanged while assigning zero to pixels which have gray values of other categories to obtain a characteristic image; and
identify connected regions in the characteristic image and determine one or more connected regions with maximum intensity to obtain the high intensity portions.

23. The apparatus of claim 22, wherein the image processor is further configured to:
analyze intensities and shapes of the connected regions identified; and
determine the section type of the specified section image based on the measuring mode and results of the analysis.

24. The apparatus of claim 22, wherein the image processor is further configured to perform a pre-processing on the specified section image to increase boundary continuity before extracting the high intensity portions in the specified section image, and a post-processing on the characteristic image to remove noise to increase boundary continuity after the characteristic image is obtained.

* * * * *